(12) United States Patent
Levernier et al.

(10) Patent No.: US 8,474,463 B2
(45) Date of Patent: *Jul. 2, 2013

(54) METHODS AND DEVICES FOR NON-ABLATIVE LASER TREATMENT OF DERMATOLOGIC CONDITIONS

(75) Inventors: Michael Levernier, San Francisco, CA (US); Greg Spooner, Kensington, CA (US); David A. Gollnick, San Francisco, CA (US); Dean A. MacFarland, Magnolia, MA (US)

(73) Assignee: Cutera, Inc., Brisbane, CA (US)

( * ) Notice: Subject to any disclaimer, the term of this patent is extended or adjusted under 35 U.S.C. 154(b) by 385 days.

This patent is subject to a terminal disclaimer.

(21) Appl. No.: 12/725,159

(22) Filed: Mar. 16, 2010

(65) Prior Publication Data
US 2010/0222853 A1 Sep. 2, 2010

Related U.S. Application Data

(63) Continuation of application No. 10/782,534, filed on Feb. 19, 2004, now Pat. No. 7,703,458.

(60) Provisional application No. 60/448,968, filed on Feb. 21, 2003.

(51) Int. Cl.
*A61B 19/00* (2006.01)
*A61B 18/20* (2006.01)

(52) U.S. Cl.
USPC ......... 128/898; 606/3; 606/9; 607/89; 607/96

(58) Field of Classification Search
USPC .................. 606/3, 9, 10–12, 131; 607/88–91, 607/96, 100–102; 128/898
See application file for complete search history.

(56) References Cited

U.S. PATENT DOCUMENTS

| | | | |
|---|---|---|---|
| 5,300,097 A | 4/1994 | Lerner et al. | |
| 5,405,368 A | 4/1995 | Eckhouse | |
| 5,527,308 A | 6/1996 | Anderson et al. | |
| 5,556,612 A | 9/1996 | Anderson et al. | |
| 5,558,666 A * | 9/1996 | Dewey et al. | 606/9 |
| 5,558,667 A | 9/1996 | Yarborough et al. | |
| 5,595,568 A | 1/1997 | Anderson et al. | |
| 5,620,478 A | 4/1997 | Eckhouse | |
| 5,626,631 A | 5/1997 | Eckhouse | |
| 5,643,334 A | 7/1997 | Eckhouse et al. | |

(Continued)

OTHER PUBLICATIONS

E. V. Ross et al., "(75) Laser Treatment of Acne Through Selective Dermal Heating," *American Society for Laser Medicine and Surgery Abstracts*, 22$^{nd}$ Annual Meeting, issue supplement 14, Apr. 10-14, 2002, pp. 23.

(Continued)

*Primary Examiner* — Ahmed Farah
(74) *Attorney, Agent, or Firm* — Morrison & Foerster LLP

(57) ABSTRACT

The invention comprises a system and method for non-ablative laser treatment of dermatologic conditions. A laser energy is transmitted to an underlying target element in the skin. The target element is heated to a temperature of at least forty degrees Celsius. In some embodiments, a pulsed, near infrared, high peak power laser energy is used. The systems and methods of the present invention may be used to treat acne, smooth wrinkles, remove hair, treat leg veins, treat facial veins, improve skin texture, decrease pore sizes, reduce rosacea, reduce "blush/diffuse redness, reduce striae, reduce scarring, or the like.

23 Claims, 15 Drawing Sheets

```
START
  │
  ▼
Irradiating an area of a patient's skin with a near infrared light
comprising a peak power of at least 10kW to cause thermal heating to an    ─ 106
underlying target element (e.g., sebaceous gland)
  │
  ▼
Maintaining the irradiating of the area for a predetermined time period    ─ 108
  │
  ▼
STOP
```

U.S. PATENT DOCUMENTS

| | | | |
|---|---|---|---|
| 5,669,916 | A | 9/1997 | Anderson |
| 5,683,380 | A | 11/1997 | Eckhouse et al. |
| 5,720,772 | A | 2/1998 | Eckhouse |
| 5,735,844 | A | 4/1998 | Anderson et al. |
| 5,752,949 | A | 5/1998 | Tankovich et al. |
| 5,754,573 | A | 5/1998 | Yarborough et al. |
| 5,755,751 | A | 5/1998 | Eckhouse |
| 5,776,127 | A | 7/1998 | Anderson et al. |
| 5,776,175 | A * | 7/1998 | Eckhouse et al. .............. 607/100 |
| 5,810,801 | A | 9/1998 | Anderson et al. |
| 5,814,041 | A | 9/1998 | Anderson et al. |
| 5,824,023 | A | 10/1998 | Anderson |
| 5,828,803 | A | 10/1998 | Eckhouse |
| 5,836,999 | A | 11/1998 | Eckhouse et al. |
| 5,849,029 | A | 12/1998 | Eckhouse et al. |
| 5,879,326 | A | 3/1999 | Godshall et al. |
| 5,885,273 | A | 3/1999 | Eckhouse et al. |
| 5,911,718 | A | 6/1999 | Yarborough et al. |
| 5,964,749 | A | 10/1999 | Eckhouse et al. |
| 5,989,267 | A | 11/1999 | Anderson |
| 6,066,130 | A | 5/2000 | Gregory et al. |
| 6,120,497 | A | 9/2000 | Anderson et al. |
| 6,126,655 | A | 10/2000 | Domankevitz et al. |
| 6,149,644 | A | 11/2000 | Xie |
| 6,162,212 | A | 12/2000 | Kreindel et al. |
| 6,174,325 | B1 | 1/2001 | Eckhouse |
| 6,183,773 | B1 | 2/2001 | Anderson |
| 6,235,016 | B1 | 5/2001 | Stewart |
| 6,273,883 | B1 * | 8/2001 | Furumoto ........................ 606/9 |
| 6,273,884 | B1 | 8/2001 | Altshuler et al. |
| 6,280,438 | B1 | 8/2001 | Eckhouse et al. |
| 6,283,956 | B1 | 9/2001 | McDaniel |
| 6,306,130 | B1 | 10/2001 | Anderson et al. |
| 6,350,261 | B1 | 2/2002 | Domankevitz et al. |
| 6,387,089 | B1 | 5/2002 | Kreindel et al. |
| 6,436,127 | B1 | 8/2002 | Anderson et al. |
| 6,511,475 | B1 | 1/2003 | Altshuler et al. |
| 6,514,243 | B1 | 2/2003 | Eckhouse et al. |
| 6,529,543 | B1 | 3/2003 | Anderson et al. |
| 6,600,951 | B1 | 7/2003 | Anderson |
| 6,605,080 | B1 | 8/2003 | Altshuler et al. |
| 6,659,999 | B1 | 12/2003 | Anderson et al. |
| 6,743,222 | B2 | 6/2004 | Durkin et al. |
| 7,276,059 | B2 | 10/2007 | Irwin |
| 7,703,458 | B2 * | 4/2010 | Levernier et al. ............. 128/898 |
| 2001/0023363 | A1 | 9/2001 | Harth et al. |
| 2002/0099094 | A1 | 7/2002 | Anderson |
| 2003/0036749 | A1 * | 2/2003 | Durkin et al. ..................... 606/3 |
| 2003/0216795 | A1 | 11/2003 | Harth et al. |
| 2004/0010300 | A1 | 1/2004 | Masotti et al. |

OTHER PUBLICATIONS

Nathan S. Uebelhoer et al., "(96) Laser Treatment of Facial Acne With a 1450 nm Diode Laser," *American Society for Laser Medicine and Surgery Abstracts*, 23$^{rd}$ Annual Meeting, issue supplement 15, Apr. 9-13, 2003, p. 29.

* cited by examiner

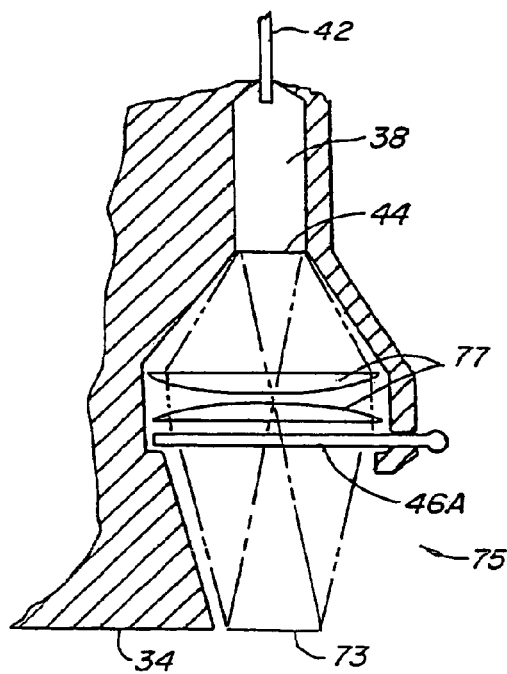
FIG. 7
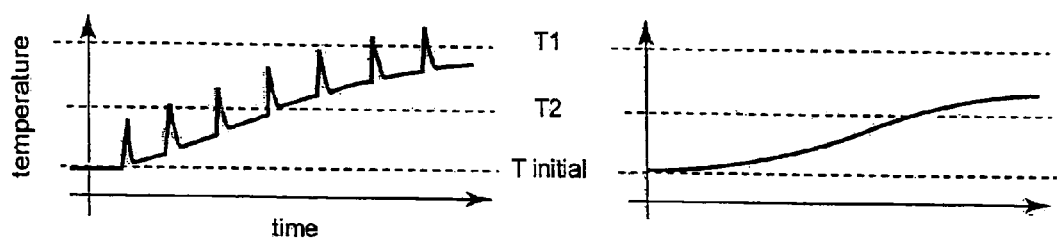
FIG. 8A
FIG. 8B

METHODS AND DEVICES FOR NON-ABLATIVE LASER TREATMENT OF DERMATOLOGIC CONDITIONS

RELATED APPLICATIONS

This application is a Continuation of U.S. patent application Ser. No. 10/782,534, filed Feb. 19, 2004, entitled METHODS AND DEVICES FOR NON-ABLATIVE LASER TREATMENT OF DERMATOLOGIC CONDITIONS, which claims the benefit from U.S. Provisional Patent Application Ser. No. 60/448,968, filed Feb. 21, 2003, entitled METHODS AND DEVICES FOR NON-ABLATIVE LASER TREATMENT OF DERMATOLOGIC CONDITIONS, all of which are incorporated herein by reference in their entirety.

BACKGROUND OF THE INVENTION

The present invention relates generally to non-ablative laser treatment of dermatologic conditions. More particularly, the present invention relates to dermatologic treatment of wrinkles, skin texturing, pore size reduction, rosacea, blush/diffuse redness, striae (e.g., stretch marks), scarring, and acne.

Million of teen-agers and young adults in the United States suffer from acne vulgaris (commonly referred to as "acne.") Acne vulgaris is a disease of the skin that results from a combination of follicular hyperkeratinization, the presence of *Propionibacterium acnes* (*p. acnes*) bacteria in the follicular canal, and excessive sebum production in the sebaceous gland. It has been suggested that elimination of any of the three factors will result in the prevention of acne vulgaris.

Acne vulgaris commonly occurs on the face, neck, back and chest where sebaceous glands are present. Normally, the lining of skin duct sheds dead cells and are transported to the skin surface by a sebum secretion from the sebaceous gland. When the duct is blocked, the dead cells and sebum accumulate and form a plug or comedo in the duct. If the plug stays below the surface of the skin, it is called a "closed" comedo or whitehead. If the plug enlarges and is exposed out of the duct, it is called an "open" comedo or blackhead.

Conventional treatments of acne vulgaris include the use of topical treatments and/or oral medications. Some common topical treatments include topical antibiotics, benzoyl peroxide (e.g., Oxy-10), Retin-A®, and the like. Some common oral medications include, oral antibiotics, Accutane, and some birth control pills.

In addition to the topical treatments and oral medications, a number of phototherapies have also been suggested for the treatment of acne vulgaris. For example, blue and ultraviolet light (UV) have been found to photoactively target the acne-associated *p. acnes* bacteria through free radical oxygen species of photoactivation of PP-IX molecules. The molecules are endogenous and in relatively high concentration in *p. acnes*. It is believed that repeated exposure to blue light may improve symptoms of acne vulgaris without the concerns associated with prolonged exposure to UV light. See Sigurdsson, V., Knulst, A. C., van Weelden, H., "Phototherapy of Acne Vulgaris with Visible Light," *Dermatology* 1997; 194: 256-260, Mills, Otto H., M A, Kligman, Albert M., MD., PhD., "Ultraviolet Phototherapy and Photochemotherapy of Acne Vulgaris," Arch Dermatol. 1978; 114: 221-223, and Papageorgiou, P., Katsambas, A., Chu, A. "Phototherapy with blue (415 nm) and red (660 nm) light in the treatment of acne vulgaris," *British Journal of Dermatology* 2000; 142:973-978. Some commentators have also suggested that *P. acnes* can be destroyed by relatively modest temperatures. See Ross, E. V. et al., "Laser Treatment of Acne Through Selective Dermal Heating," *Lasers in Surgery and Medicine,* 2002, Supplement 14:23.

Unfortunately, none of the conventional therapies have proven to be completely successful in treating acne vulgaris. Therefore, what is needed are effective, non-ablative solution for treating acne vulgaris, and other dermatologic conditions.

BRIEF SUMMARY OF THE INVENTION

The invention provides improved systems and methods for non-ablative laser treatment of an exposed skin surface with a laser light energy.

In one aspect, the present invention provides a method of performing a non-ablative dermatologic treatment. The method comprises transmitting a laser energy into a target tissue, such as a sebaceous gland, blood vessel, melanocyte. The laser energy is continued until the target tissue is heated to a temperature of at least forty degrees Celsius.

In some exemplary embodiments, the non-ablative dermatologic treatments may be used for the reduction of wrinkles, hair removal or reduction, leg vein treatment, facial vein treatment, improvement of skin texture, decrease of pore size, reduction of rosacea, reduction of "blush"/diffuse redness, treatment of striae, reduction of scarring, and the like.

The target tissue may be heated and maintained at a selected temperature for a predetermined time so as to achieve the desired result. The predetermined time may vary depending on the number of pulses, the maximum desired temperature reached, and/or the desired result, but is usually between one second and twenty seconds, but may be as high as five minutes.

A wavelength for the laser energy is chosen such that the target tissue is heated, without undue heating of the surrounding tissue. In one embodiment, a near infrared laser (e.g., a laser beam having a wavelength between 800 nm and 1200 nm, and typically 1064 nm) is pulsed to thermally treat the target tissue, while maintaining the epidermis at a safe temperature.

In some embodiments, the laser energy is transmitted into the target tissue through a series of high peak power pulses. The peak power pulses are typically above approximately 10 kW, and are typically about 14 kW. The laser energy may have short pulse operations between approximately 100 microseconds and 3000 microseconds so as to deliver a large amount of energy into the target tissue in a short amount of time. The pulses may have a repetition rate between approximately 2 Hz and 12 Hz. The laser pulses may have a fluence of at least about 8 Joules per square centimeter, and typically between 10 Joules per square centimeter and 20 Joules per square centimeter, and preferably between approximately 12 Joules per square centimeter and approximately 17 Joules per square centimeter.

In one embodiment, the present invention provides a method of performing a non-ablative phototherapy on a sebaceous gland to treat a sebaceous gland disorder, such as acne vulgaris. The method comprises transmitting a laser energy into the sebaceous gland. The sebaceous gland is heated to a temperature of at least forty degrees Celsius, and typically between approximately forty-five degrees Celsius and approximately fifty degrees Celsius. The sebaceous gland is maintained at the selected temperature for a predetermined time so as to treat the acne vulgaris. The predetermined time may vary depending on the number of pulses and/or the maximum desired temperature reached, but is usually between 1 seconds and 20 seconds.

A wavelength for the laser energy is chosen such that the sebaceous glands are heated, without undue heating of the surrounding tissue, such as the epidermis. In one embodiment, a near infrared laser (e.g., a laser beam having a wavelength between 800 nm and 1200 nm, and typically 1064 nm) is pulsed to thermally treat the sebaceous gland, while maintaining the epidermis at a safe temperature. Embodiments of the present invention may use transient heating of sebaceous gland absorbers (e.g., melanin and hemoglobin) and/or bulk heating through weak absorption of the laser light and thermal diffusion from the sebaceous gland absorbers and other absorbing structures in the epidermis and dermis (e.g., water and hemoglobin) to thermally treat the sebaceous gland.

In some embodiments, the laser energy is transmitted into the sebaceous glands through a series of high peak power pulses. The peak power pulses are typically above approximately 10 kW, and are typically about 14 kW. The laser energy may have short pulse operations between approximately 100 microseconds and 3000 microseconds so as to deliver a large amount of energy into the tissue in a short amount of time. The pulses may have a repetition rate between approximately 2 Hz and 12 Hz. The laser pulses may have a fluence of at least about 8 Joules per square centimeter, and typically between 8 Joules per square centimeter and 20 Joules per square centimeter.

Applicants believe that heating of the sebaceous gland to above forty degrees Celsius may treat acne vulgaris by reducing the *p. acnes* population in and around the sebaceous gland, effect the rate of sebum secretions from the sebaceous gland, and/or may damage or destroy the sebaceous gland.

In another method of treating acne vulgaris, a method of the present invention comprises irradiating an area of a patient's skin with a near infrared light comprising a peak power of at least 10 kW to cause thermal heating to an underlying sebaceous gland. Irradiation of the sebaceous gland is continued until a predetermined temperature is reached. The irradiation is maintained for a sufficient time period to treat the acne vulgaris.

Similar to above, the irradiation of the area is typically carried out with a series of pulsed laser beam at a moderate rep rate of between approximately 1 Hz and approximately 10 Hz. The temperature of the sebaceous gland is typically raised to a temperature of at least forty degrees Celsius. The high peak power provides a large amount of energy directly into the sebaceous gland so as to cause a fast temperature spike in the sebaceous gland, while causing little damage to the surrounding tissue.

In a further aspect, the present invention provides a system to for non-ablative laser treatment of a patient's skin. The system includes a laser source that generates a high peak power near infrared (NIR) laser. A controller is coupled to laser source to control delivery of the laser to the patient's skin. A handpiece can be coupled to laser via an umbilical cord to direct the laser to the target tissue (e.g., sebaceous gland, vein, melanocyte) in the patient's skin. The systems of the present invention may be used to carry out any of the methods described herein.

In one embodiment, the system of the present invention has a power supply architecture that allows for a pulsed high peak power operation. The system may generate peak power laser pulses above approximately 10 kW, and typically about 14 kW. The controller and laser may be configured to produce short pulse operations between approximately 100 microseconds and 3000 microseconds, with the repetition rate between approximately 2 Hz and 12 Hz. The laser pulses may have a fluence of at least about 8 Joules per square centimeter, and typically between 10 Joules per square centimeter and 20 Joules per square centimeter, and preferably between 12 Joules per square centimeter and 17 Joules per square centimeter.

The laser source will typically be configured to emit a light energy having a wavelength of 1064 nanometers. The laser is optically coupled to the tissue of the patient so that the light energy is transmitted to an underlying sebaceous gland. In one embodiment, the system comprises a high power, free running pulse Neodymium:Yttrium Aluminum Garnet laser ("Nd:YAG").

In yet another aspect, the present invention provides a method of smoothing wrinkles. The method comprises transmitting a laser energy into a target tissue in the skin. The target tissue is heated to a temperature of at least forty degrees Celsius so as to effect a smoothing of the epidermis. The methods of smoothing wrinkles may follow similar procedures as the other methods described herein and may use similar systems to carry out the method.

In a further aspect, the present invention provides a method of improving a texture of skin. The method comprises transmitting a laser energy into a target tissue in the skin. The target tissue is heated to a temperature of at least forty degrees Celsius so as to texturize the epidermis.

In a further aspect, the present invention provides a method of improving a reducing a pore size. The method comprises transmitting a laser energy into a target tissue in the skin. The target tissue is heated to a temperature of at least forty degrees Celsius so as to reduce a size of a pore.

For a further understanding of the nature and advantages of the invention, reference should be made to the following description taken in conjunction with the accompanying drawings.

BRIEF DESCRIPTION OF THE DRAWINGS

FIG. 7 is a simplified cross-sectional view of an alternative embodiment of a handpiece of an acne treatment system of FIG. 3F in which the handpiece is configured to permit the practitioner to see the skin area being treated;

FIG. 8A is a thermal profile of a strong absorber of NIR light near or at a target element, such as the sebaceous gland;

FIG. 8B is a thermal profile of dermal tissue that is remote from the strong absorber of FIG. 8A;

DETAILED DESCRIPTION OF THE INVENTION

The present invention provides non-ablative laser treatments of dermatologic conditions. The systems and methods rely on phototherapy at specific ultraviolet (UV) to near infrared (IR) wavelengths of non-coherent light to carry out the treatments. Examples include the treatment of wrinkles, hair removal or reduction, leg vein treatment, facial vein treatment, improvement of skin texture, decrease of pore size, reduction of rosacea, "blush"/diffuse redness, striae, scarring, and the like. As can be appreciated, the apparatus and methods described herein are applicable in dermatologic and other directly accessible tissues, for example any exposed tissue. Information on assignees prior hair removal system can be found in U.S. Pat. No. 6,666,856, the complete disclosure of which is incorporated herein by reference in its entirety.

For ease of reference, the remaining discussion focuses on the treatment of the sebaceous gland for purposes of treating acne. Those of ordinary skill should recognize that the systems and methods of the present invention are equally applicable to other non-ablative treatments of other target tissue in the skin that are described herein.

In one particular embodiment, the present invention provides methods and systems that use laser light to thermally treat the sebaceous glands to thermally treat acne vulgaris and other forms of active acne. The present invention includes a laser light that has treatment wavelength(s) and power levels based on an understanding of a photodestructively targeted sebaceous gland and/or acne bacterium, *p. acnes*.

In one embodiment, the present invention may utilize a solid state laser system based on a 1064 nanometer wavelength light source. One useful embodiment is the CoolGlide Vantage™, sold by Altus Medical, Inc. It should be appreciated, however, that the present invention is not limited to such lasers, and other lasers, such as the Altus Excel, Genesis, or other different lasers that have different laser parameters may be used to perform a non-ablative laser treatment of the skin (e.g., treat acne), without departing from the scope of the present invention.

Figure 1:
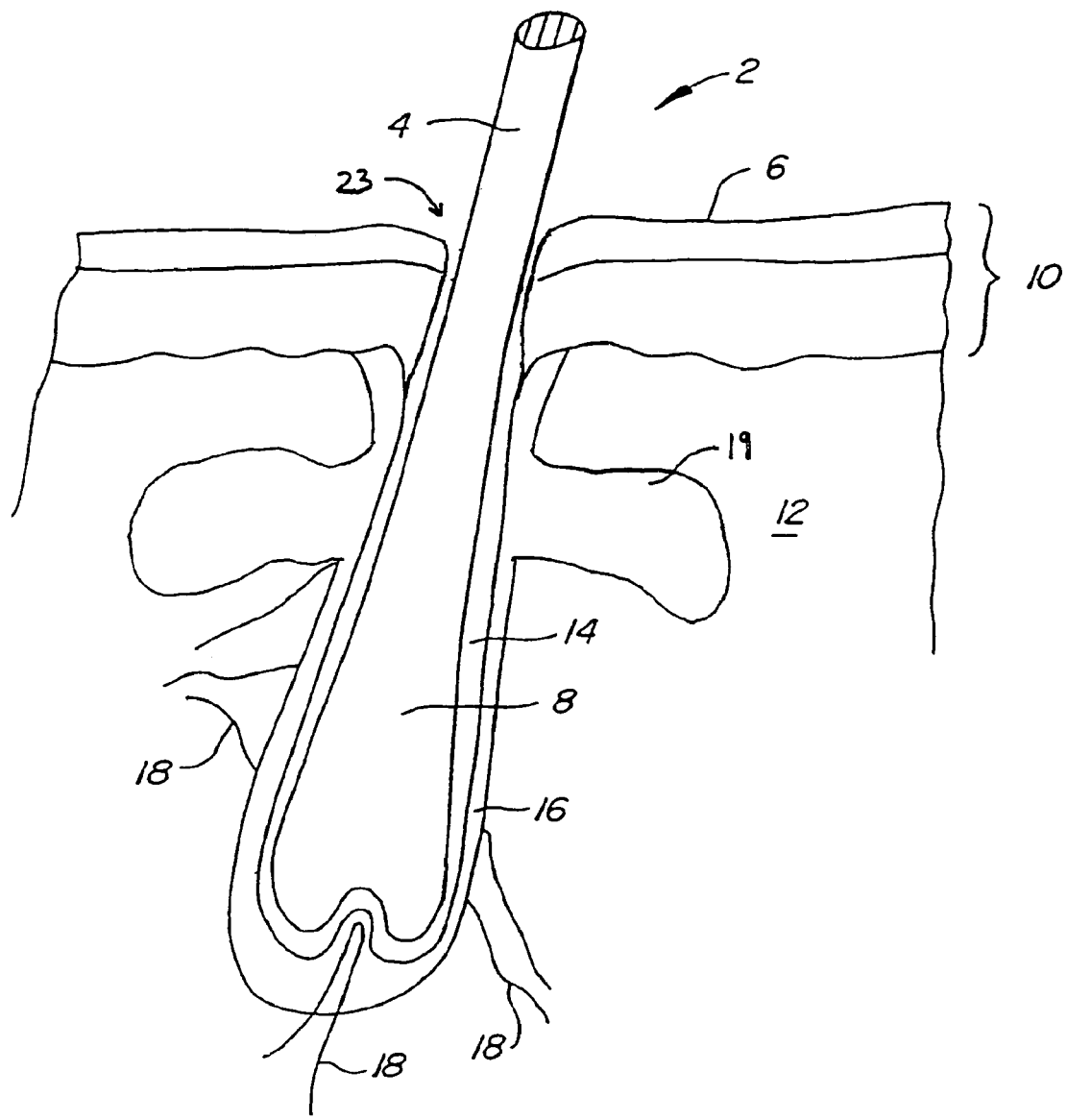
FIG. 1 is a simplified cross-sectional view of a hair follicle having a sebaceous gland.

FIG. 1 illustrates, in simplified form, a hair 2 including a shaft 4 extending above skin surface 6 and a root 8 extending below the skin surface. The root 8 passes through epidermis 10 into dermis 12 with the base of the root, or papilla, being about 4 mm below surface 6. Root 8 is housed within hair follicle 14 and is surrounded by various tissues including connective tissue sheath 16 and blood vessels 18. Follicle 14 includes a sebaceous gland 19 which is below an opening 23 in follicle 14. Sebaceous gland 19 is typically between approximately 0.3 mm and approximately 2.0 mm below surface 6, but will vary depending on its location on the body.

Because melanin is present in epidermis 10, with darker skin types having more melanin than lighter skin types, the wavelength of the therapeutic laser should be long enough so that absorption is low for the moderate concentrations of melanin in the epidermis to permit most of the light to pass through epidermis 10 to the underlying sebaceous gland 19. Therefore, it is preferred to use a laser source that produces a laser of wavelengths in the 800 nanometer to 1200 nanometer range. One useful embodiment is a solid state neodymium-doped YAG laser (Nd:YAG) based on a wavelength of 1064 nanometers, because it is a relatively efficient source and the technology is well developed and readily available. The long wavelength of 1064 nanometers is believed to give physicians the flexibility to treat a greater variety of skin types.

Figure 2A:
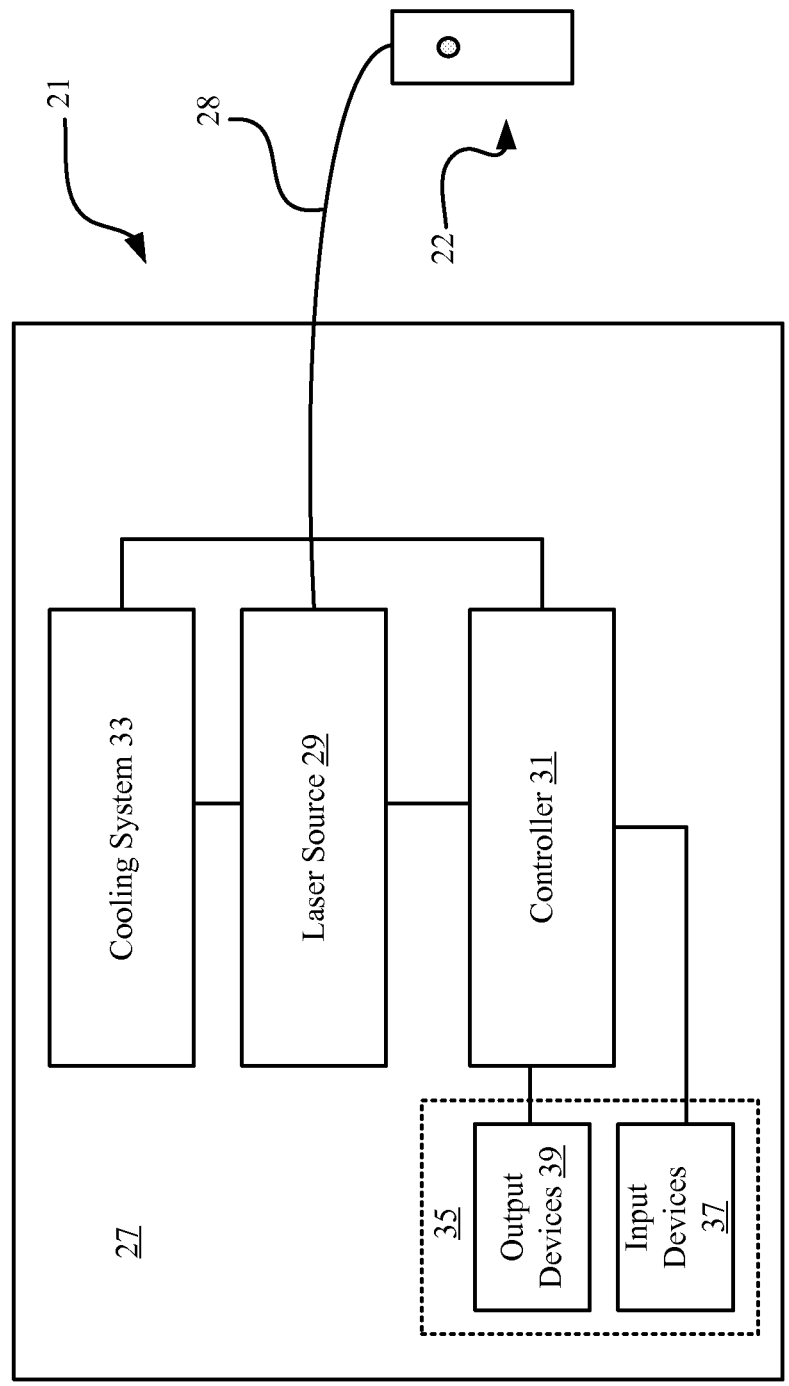
FIG. 2A is a schematic representation of an acne treatment system according to the present invention.

FIG. 2A schematically illustrates one useful embodiment of an acne treatment assembly 21 of the present invention. Acne treatment assembly 21 includes a laser control console 27 that houses a laser source 29, such as the Nd:YAG laser. Laser source 29 is in communication with a controller 31 that typically includes a processor that stores software for controlling the delivery of the therapeutic laser light. The processor is in communication with a random access memory (RAM) and a read only memory (ROM), and other conventional computer memory. Other tangible media in addition to RAM and ROM include floppy disk drives, CD drives, and hard disk drives may be coupled to the processor, if desired. Optionally, controller may be include a timer that times the laser treatment and/or a pulse counter that counts the number of delivered pulses. Controller 31 may optionally be configured to stop delivery of the laser energy in response to a measured treatment time or if a threshold number of pulses are delivered.

A laser energy applicator, such as a handpiece 22 can be attached to laser source 29 (and/or controller 31) with an umbilical cable 28 so as to deliver the laser energy to the patient's skin. If desired, an optional cooling system 33 may be coupled to laser source 29 and handpiece 22 to provide cooling to the laser source and to the patient skin. Optionally, a temperature sensor may be coupled with handpiece 22 and controller 31 for measuring a temperature of the skin surface.

A user interface 35 may be coupled to console 27 and includes one or more input devices 37 and output devices 39 to allow for input of commands and to provide information to a user of acne treatment assembly 21. User interface 35 may have a number of input devices 37 to allow a user to change the delivery parameters of the laser. For example, in one useful embodiment, inputs 37 include a laser-pulse duration input. The laser pulse duration may typically be chosen to be between 100 microseconds and 1000 microseconds. User interface 35 may also include a laser-pulse fluence input that may be adjusted as high as 300 J/cm$^2$, although for the methods of the present invention, the typical fluence is between approximately 8 J/cm$^2$ and approximately 20 J/cm$^2$, and preferably about 13 J/cm$^2$. A repetition rate input may be provided that allows the repetition rate to be varied from a single shot to a repetition rate of about 12 Hz. For the methods of the present invention, a typical repetition rate may be 2 Hz, 3 Hz, 4 Hz, 5 Hz, 6 Hz, or 7 Hz. depending on the other laser parameters, practitioner expertise, the size of the area being treated, and other factors. Optionally, input device 37 may include a footswitch (not shown) and/or a button on handpiece 22 for controlling the delivery of laser light pulses from handpiece 22 to skin surface 6. As can be appreciated, other inputs may also be provided that allow other laser variables to be controlled. The above laser parameters are merely non-limiting examples of fluence, pulse durations and repetition rates that may be used with the present invention. The laser parameters may differ depending on practitioner expertise, treatment area, and patient response, and would still be within the scope of the present invention.

One or more output devices 39 provide the user with visible or audible information, such as the temperature of a cooling surface on the handpiece, an optimal laser pulse actuation rate, the selected laser-pulse duration, selected repetition rate, selected fluence, etc.

In one preferred embodiment user interface 35 includes the following input devices and output devices: a keyswitch to start the system and turn it off, standby and ready buttons to select the state of operation, controls to select fluence level, pulse width and repetition rate, and emergency-off button; and has the option of displaying the following information: laser and handpiece status (ready/not ready), laser emission indicator, pulse counter, selected fluence, selected repetition rate, and selected pulse duration.

Figure 2B:
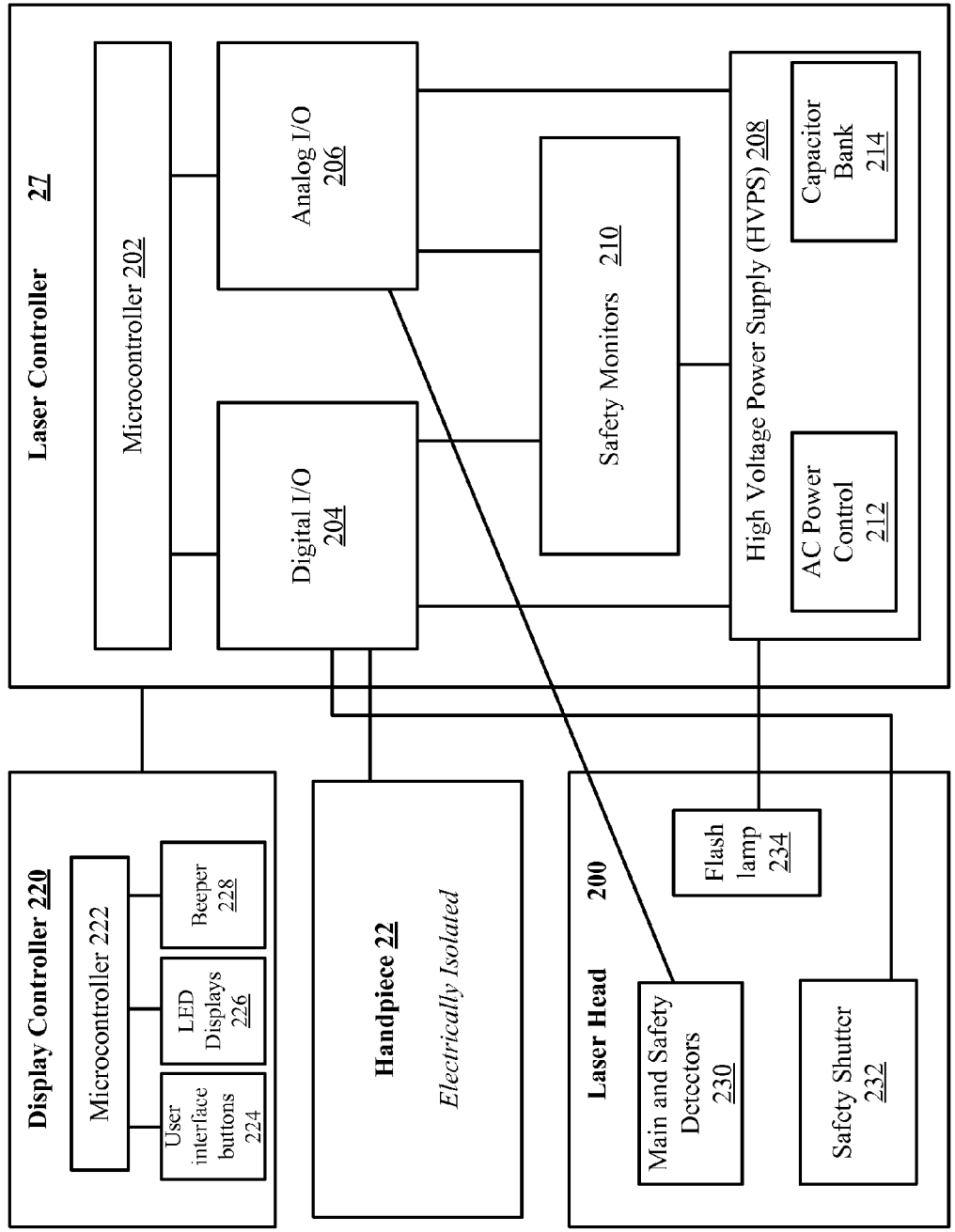
FIG. 2B is a functional block diagram of components of a system of the present invention.

Referring now to FIG. 2B, shown is a simplified functional block diagram of another non-limiting embodiment of system 21. FIG. 2B illustrates laser controller 27, an output device or display controller 220, handpiece 22 and a laser head 200. Laser controller 27 comprises a microcontroller 202 that is coupled to digital input/output 204 and analog input/output 206 assemblies. A high voltage power supply (HVPS) 208 is coupled to the input/output 204/206 through one or more safety monitors 210. In the illustrated embodiment, HVPS 208 includes an AC power control 212 and a capacitor bank 214.

Figure 2C:
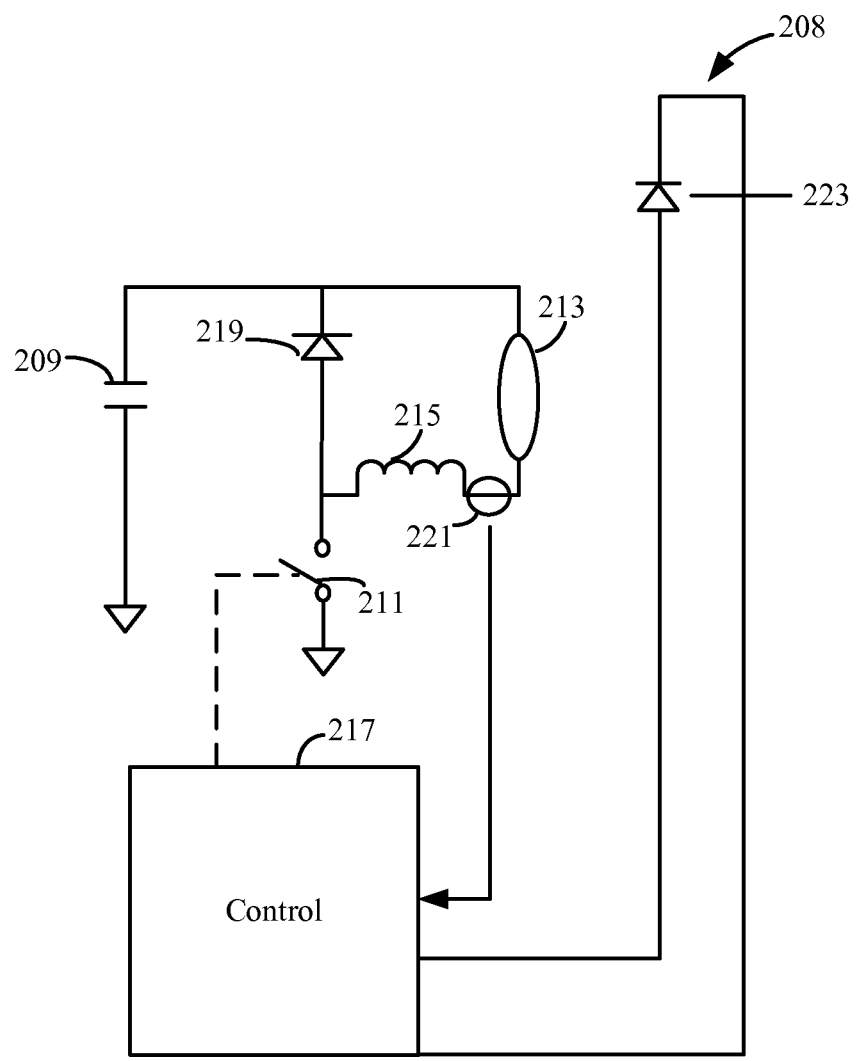
FIG. 2C illustrates one embodiment of a power supply or laser source that may be used with the system of the present invention.

FIG. 2C illustrates one particular embodiment of a power supply 208 that may be used with the system of the present invention. Power supply 208 may be controlled by a chopper circuit with an inductive filter element that operates in a pulse width modulated current controlled mode. An energy storage capacitor 209 may be charged to a level that allows a desired energy to be delivered without an unacceptable lamp voltage droop at the desired current. A switch 211 is closed which ramps up current through lamp 213, inductor 215, and switch 211. When the appropriate current is reached, control circuit 217 turns off switch 211 and the current flow diverts to a diode 219. The current flow decays to an appropriate level (typically 75% of the peak value), the control circuit 217 again turns on switch 211 and the cycle repeats until a pulse creates a slight ripple in the pulse. A current sensor 221 and photodiode 223 are used independently or in concert to control the optical power delivered to the skin. Also, as one of skill in the art would recognize other power supply circuits such as reservoir discharge circuits or pulse forming networks could also be used to drive lamp.

Referring again to FIG. 2B, a display controller 220 is coupled to laser controller 27 to provide outputs to the practitioner. Display controller 220 may comprise a separate controller 222 to process control signals from laser controller 27 and may be in communication with user interface buttons 224, LED displays 226 and/or audio outputs, such as beeper 228.

Laser controller 27 is in communication with handpiece 22 and laser head 200 so as to deliver the non-ablative laser treatment to the patient's skin. Handpiece 22 may be coupled to digital input/output 204 and may be electrically isolated. Laser head 200 may include main and safety detectors 230 that are coupled to analog input/output 206. A safety shutter 232 may be coupled to digital input/output 204. A flash lamp is coupled to HVPS 208 to deliver the laser energy to the patient's skin.

Figure 3A:
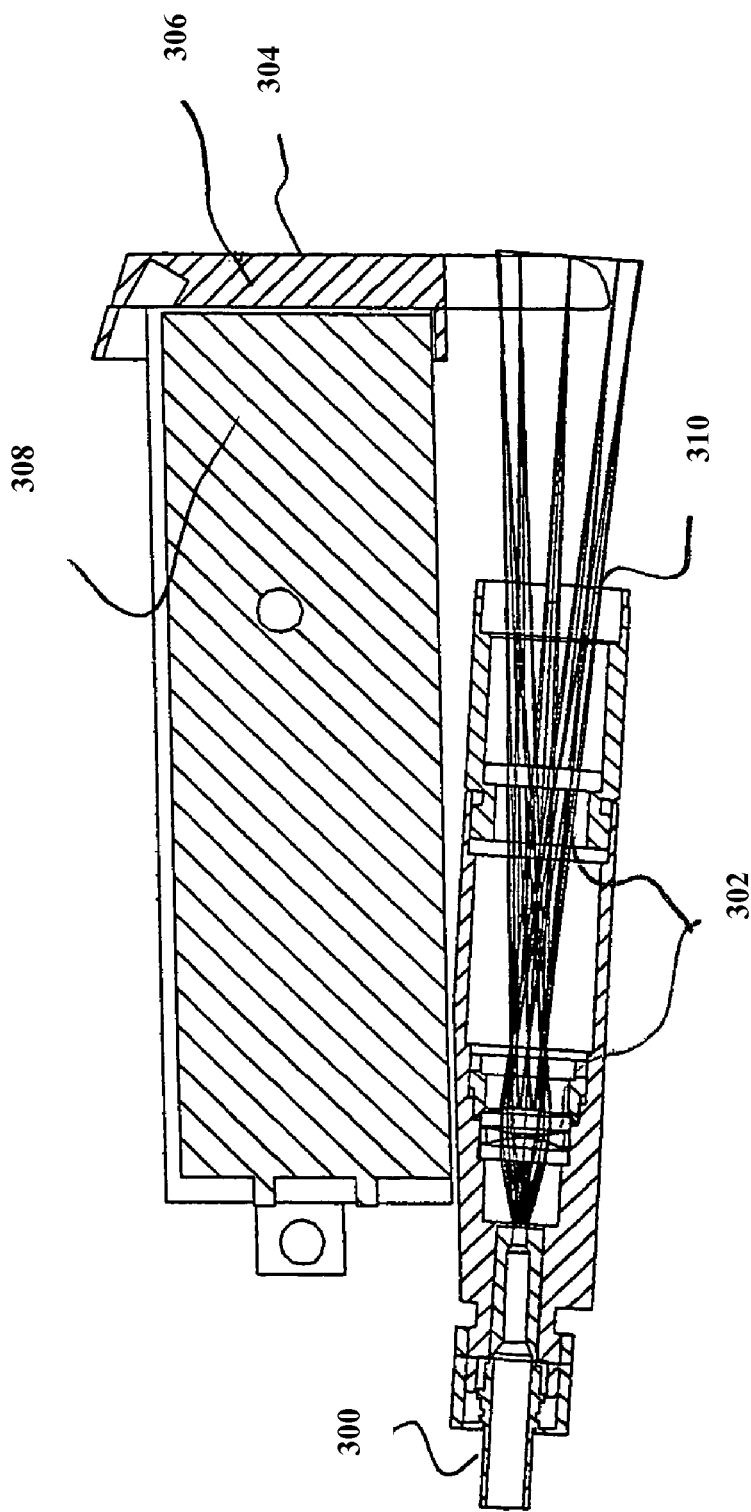
FIGS. 3A to 3E schematically illustrate five non-limiting examples of handpieces that may be used with the systems of the present invention.
Figure 3B:
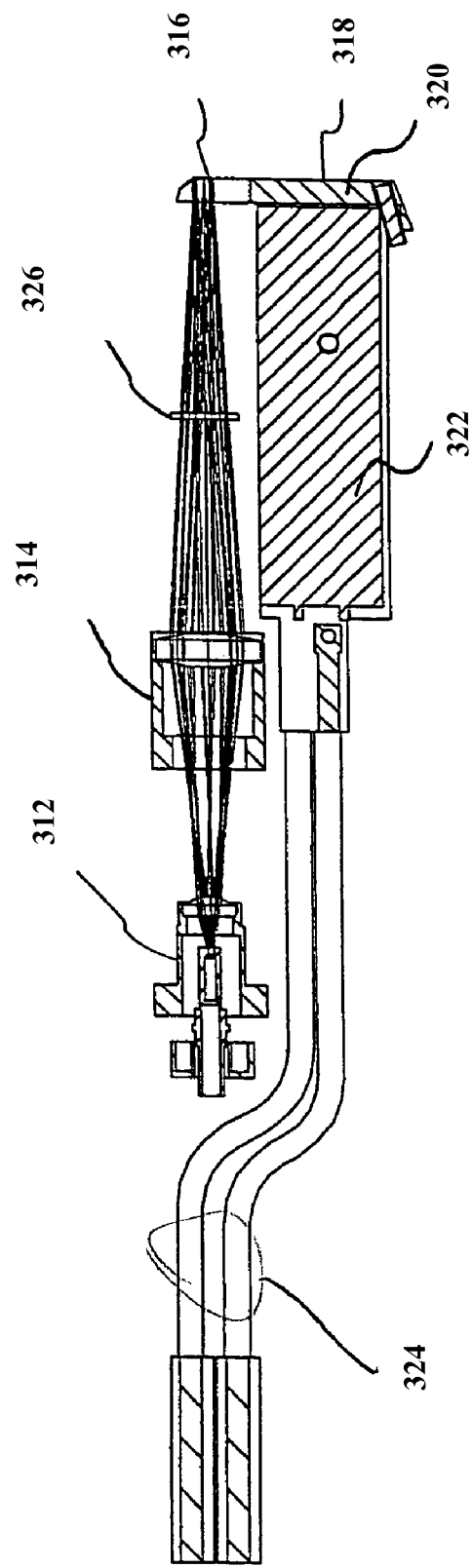
Figure 3C:
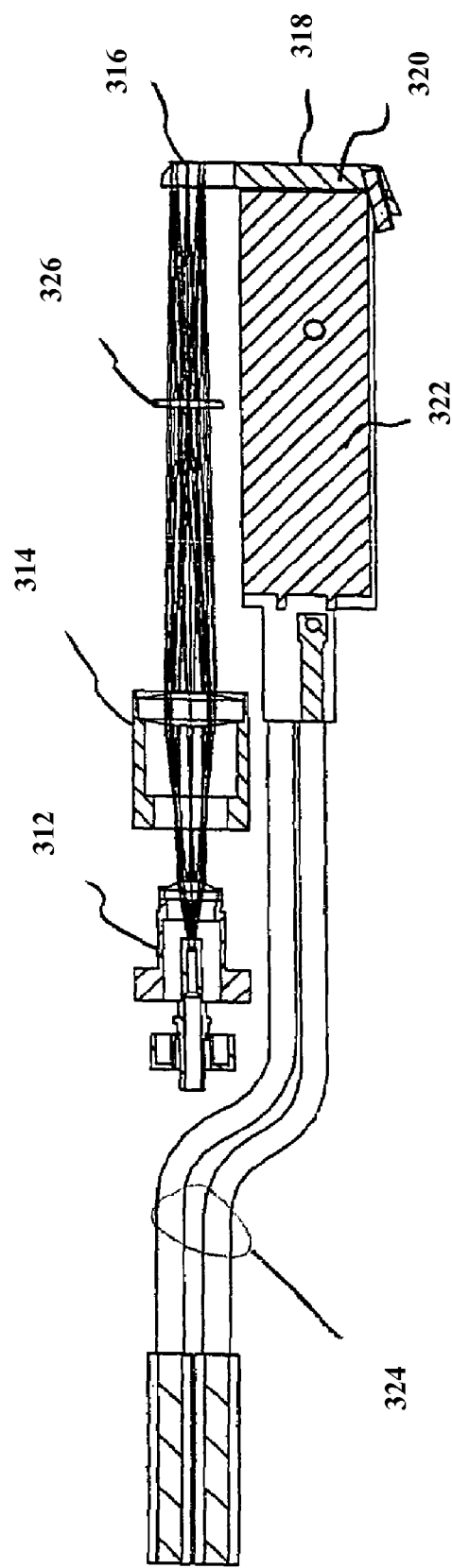
Figure 3D:
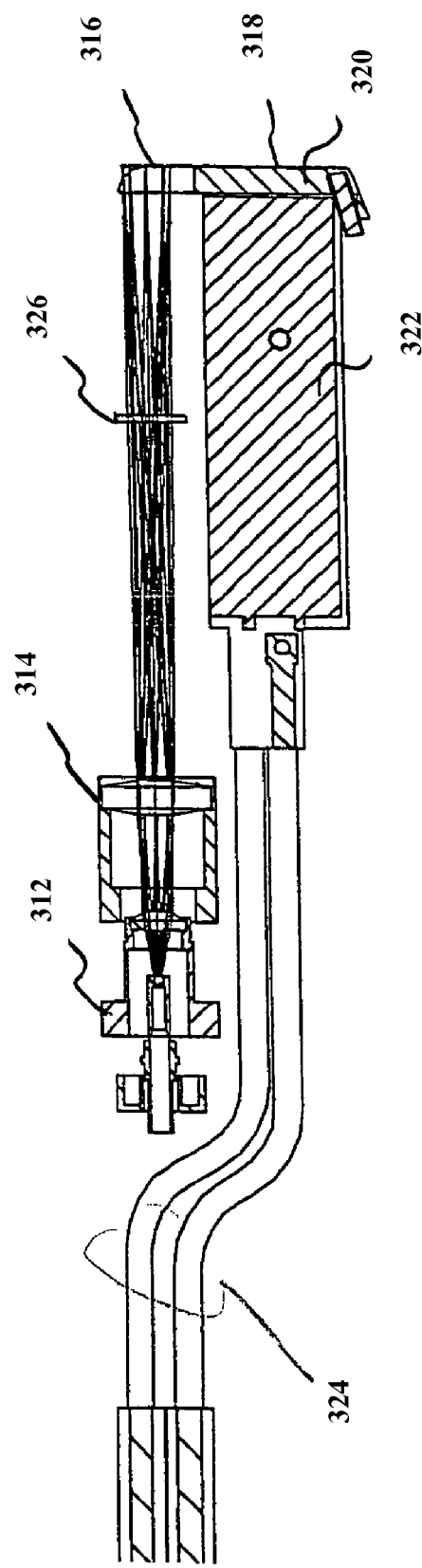
Figure 3E:
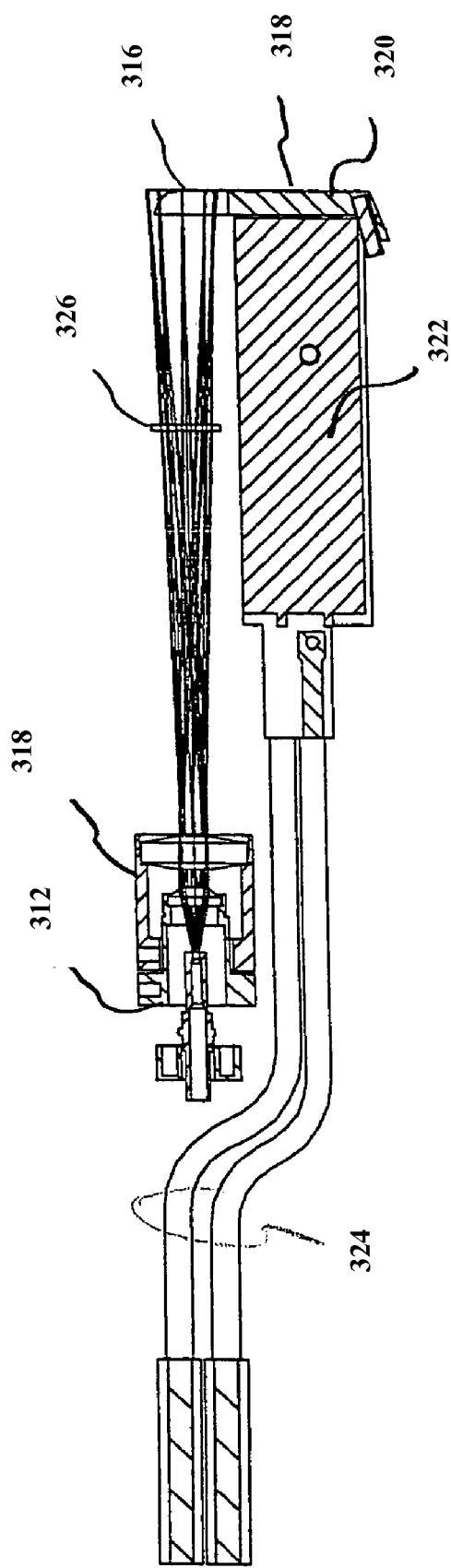

Some non-limiting examples of elements of handpieces 22 that may be used with the present invention are schematically illustrated in FIGS. 3A to 3E. In the illustrated embodiment of FIG. 3A, laser light exits a multimode fiber assembly 300 in the handpiece and may be expanded by a fixed or variable position two-element beam expander telescope. FIG. 3A shows a system which was used in the past which has a fixed position two-element 302 beam expander telescope. The position of the elements of the beam expander telescope whether fixed or variable, may be designed to place an image plane at the skin treatment surface. This treatment plane may be coincident with the cooling plane 304 defined by the thermally conducting patient contact surface 306. Optionally, the patient contact surface is thermally coupled to a water-cooled thermoelectric cooler (TEC) unit 308. Coolant circulates from the handpiece to the hot side of the TEC. An optically transparent window 310 protects the optical components from contamination. This window may be recessed from the patient contact surface and may be user-replaceable. For additional discussion of such a recessed window, see example, see U.S. Pat. No. 6,485,484 B1, which is incorporated herein by reference.

FIGS. 3B-3E illustrate elements of an embodiment of a handpiece having a variable position two-element beam expander telescope, having a first element 312 and a second element 314. The position of the lens element 312 relative to lens element 314 corresponds to a spot size at a treatment area. The position of elements 312 and 314 in FIG. 3B corresponds to a 3 mm spot, size while the positions shown in FIG. 3C, FIG. 3D and FIG. 3E correspond to spot sizes of 5 mm, 7 mm and 10 mm respectively. Each of these positions of the elements 312 and 314 may be designed to place an image plane at the skin treatment surface. This treatment plane 316 may be coincident with the cooling plane 318 defined by the thermally conducting patient contact surface 320. Optionally, the patient contact surface is thermally coupled to a water-cooled thermoelectric cooler (TEC) unit 322. Coolant circulates in flow tubes 324 from the handpiece to a hot side of the TEC. An optically transparent window 326 protects the optical components from contamination. This window may be recessed from the patient contact surface and may be user-replaceable.

Figures 3F, 3G, 4A, 4B:
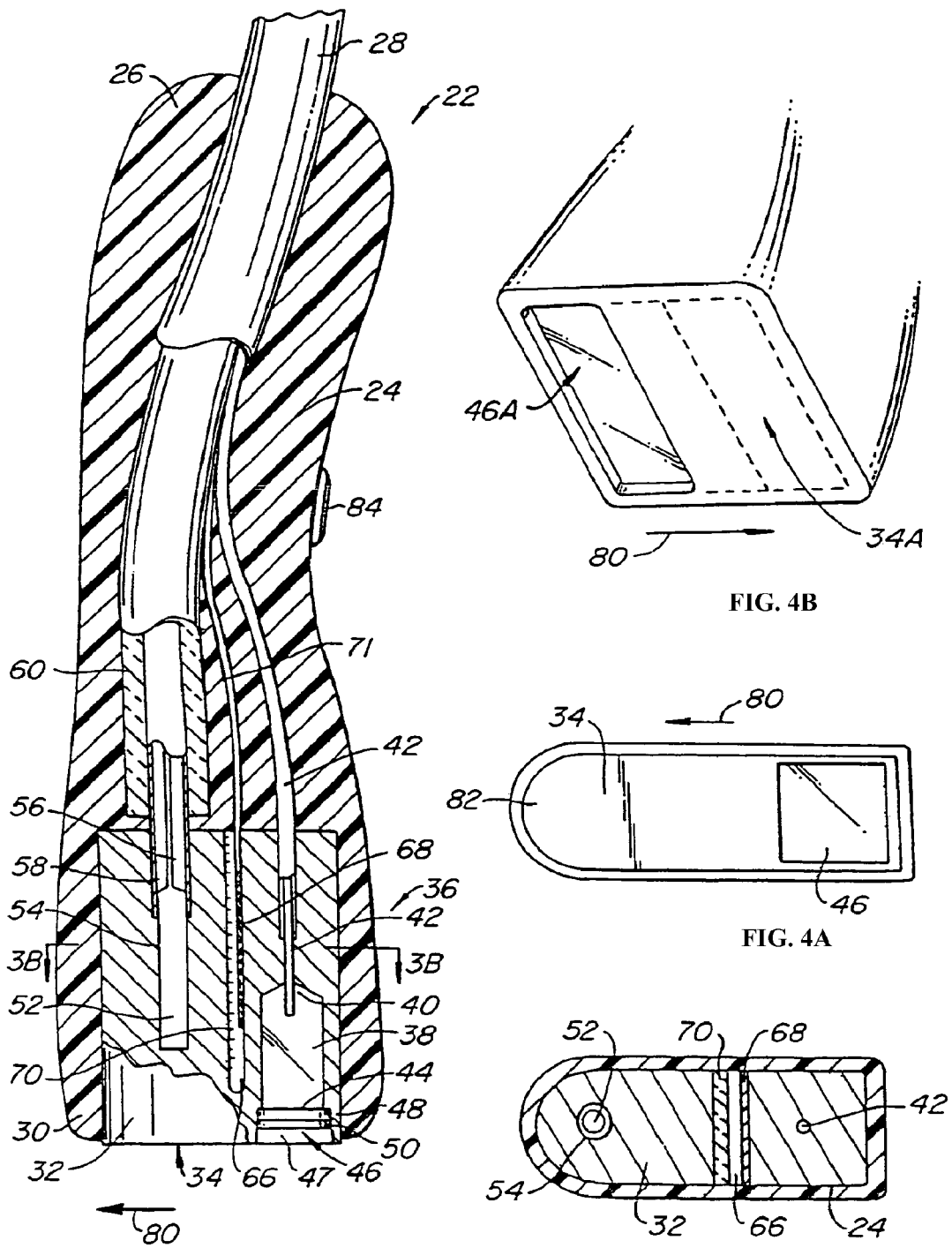
FIG. 3F is a simplified side view of a handpiece of FIG. 2A with portions broken away to show internal detail.
FIG. 3G is a simplified cross-sectional view taken along line 3B-3B of FIG. 3F.
FIG. 4A is a bottom plan view of the handpiece of FIG. 3F.
FIG. 4B is an overall view of the lower end of an alternative embodiment of the acne treatment device of FIG. 3F.

Referring now to FIG. 3F, an alternative embodiment of handpiece 22 is illustrated. Handpiece 22 includes a hand-grippable body 24 having an upper or outer end 26 into which an umbilical cable 28 passes and optionally has a lower or front end 30 that houses a formed block 32. Block 32 may be made of aluminum and may have various cavities to provide various features and functions as described herein.

As shown in FIGS. 3F and 3G, block 32 may optionally define a contact surface 34 that may be configured to contact and pre-cool epidermis 10 and surrounding tissue during and/or prior to irradiation. Surface 34 may be a low friction, high lubricity surface to help prevent bonding between the contact surface and the skin as the handpiece is moved in the direction of arrow 80. As will be described below, in some embodiments, handpiece 22 may be configured to be spaced from the surface 6 of the patient's skin.

Aluminum block 32 also houses a radiation source 36. Radiation source 36 includes a reflective chamber 38, in this embodiment having a square cross-sectional shape, but in other embodiments, may be rectangular, circular, or the like. Reflective chamber 38 has its walls covered with a highly reflective material, such as gold; the material is chosen for its reflective qualities for the particular wavelength radiation to be used. Other materials, such as dielectric layers combined with high-reflectivity metals, could also be used. Chamber 38 has an optical fiber entrance 40 to permit an optical fiber 42, or a bundle of optical fibers, to extend into chamber 38 for delivering the therapeutic laser light. The opposite end of chamber 38 has an exit aperture 44 covered by a recessed window 46. Recessed window 46 is spaced apart from optional contact surface 34 by a distance or gap 47, such as about 1 mm to 3 mm (0.04 inches to 0.12 inches). Recessed window 46 includes an inner window 48, typically permanently or semi-permanently mounted to aluminum block 32 at exit aperture 44, and an outer window 50. Outer window 50 is typically removably secured in place by the use of a clip, or other suitable means (not shown). Windows 48, 50 may be made of a suitable material, such as fused silica, although other materials, such as optical glasses, could also be used. By the use of inner and outer windows 48, 50, if outer window 50 is damaged, it can be easily replaced by the user.

In some methods, it may be desirable to cool contact surface 34. In one configuration, contact surface 34 may be cooled through the use of a coolant evaporator 52 house within a blind bore 54 formed in aluminum block 32. The coolant, which may be of various commercially available types, commonly Freon® or other fluorinated hydrocarbons, is directed to evaporator 52 through a coolant liquid line 56 and is recycled back to a refrigerant compressor 62 through a coolant vapor return line 58. Line 58 coaxially houses coolant liquid line 56, line 58 being housed within thermal insulation 60. Lines 56, 58 and insulation 60 pass through umbilical cable 28 to a refrigerant compressor in associated with control console 27.

A separation slot 66 is made between that portion aluminum block 32 used to cool surface 34 and that portion of the block used for radiation source 36. An electrical, typically resistive, heating element 68 is positioned along one wall of slot 66, the right wall as shown in FIGS. 3F and 3G, while the other, left wall is covered with thermal insulation 70. Heating element 68 is connected to console 27 through a conductor 71 extending along umbilical cable 28. In lieu of resistive heating element 68, the hot side of a thermoelectric type of heating element, may also be used.

As an alternative to the above cooling system, contact surface 34 can be cooled by a thermoelectric, Peltier device instead of the coolant evaporator. A more complete description of the use and advantages of the cooling system and different cooling systems may be found in commonly owned U.S. Pat. No. 6,485,484 B1, the complete disclosure of which is incorporated herein by reference. It should be appreciated however, that many of the non-ablative dermatologic laser treatments of the present invention do not cool the patient's skin.

Figure 5A:
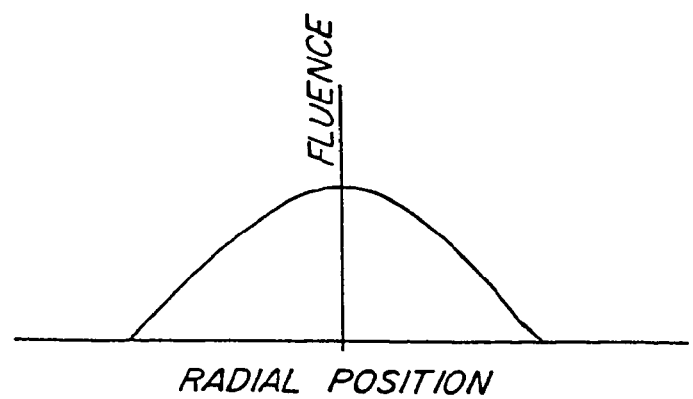
FIG. 5A is a theoretical plot of fluence versus radial position for a diverging beam.
Figure 5B:
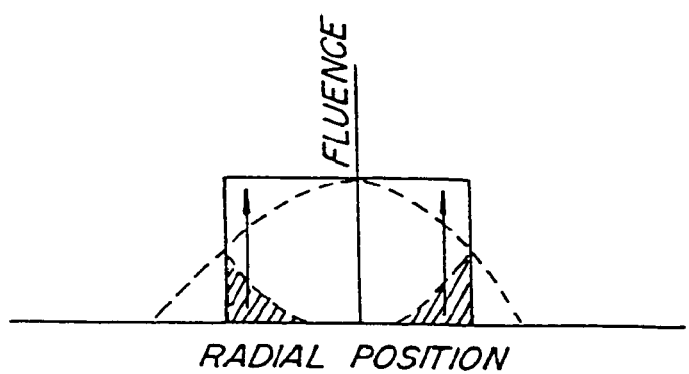
FIG. 5B shows an idealized plot of how to square off or equalize the fluence of the beam of FIG. 5.
Figure 6:
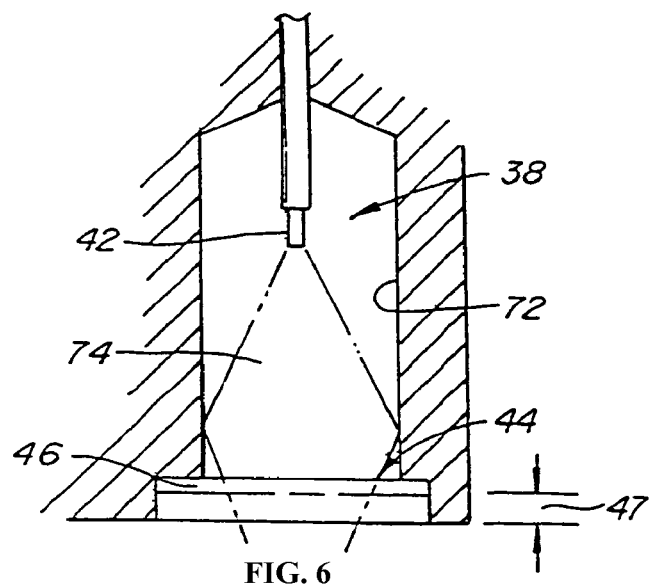
FIG. 6 is a simplified view of the radiation source of FIG. 3F showing how radiation is reflected from the walls of the reflective chamber to help equalize radiation intensity and reduce hot spots.

Referring now to FIGS. 4 to 6, treatment of the target tissue, such as the sebaceous gland, should cause thermal damage to sebaceous gland 19 but not substantial damage to surrounding tissue, such as blistering to the skin. To do so, the energy per unit area (fluence) of the laser beam 74 at skin surface 6 must be controlled. Part of the control of the fluence requires that the distance between skin surface 6 and the end of optical fiber 42 be controlled because beam 74 expands as it passes through reflective chamber 38. As such, in one configuration, front end 30 of handpiece 22 is spaced between approximately 1 cm and 2 cm from the surface of the patient's skin. The distribution of energy across the laser beam at skin surface 6 should be substantially constant so that no hot spots, which could cause local damage to the epidermis, are created. Also, the individual exposure sites should fit tightly together, commonly called a tiled effect, so that there is little or no overlapping of the exposure sites and, at the same time, little or no area is left unexposed. The simplest shape that meets this tiling requirement is a rectangle. Other shapes can create a tiled pattern but they have other drawbacks. Reflective chamber 38 and window 46 both have square cross-sectional shapes for efficient and effective treatment.

FIG. 4b illustrates an alternative embodiment of the invention in which window 46A is rectangular having a width about three times its length and handpiece 22 is moved in the direction of arrow 80. In this case contact surface 34A would have a width about equal to the width window 46A. However, the length of contact surface 34A is, like in the embodiment of FIG. 4A, about twice the length of window 46A based on the premise that the interval between actuation of fire button 84 (FIG. 3F) will be equal to one-half the length of time it is desired to apply equal surface 34A to the skin surface to properly cool the skin surface.

FIG. 5 illustrates a graph of fluence versus radial position for a diverging beam, such as from optical fiber 42. What is desired is to square off the graph to equalize the fluence over the beam spot. This is suggested in FIG. 5A in which those portions of the beam at the edges are reflected or folded over back into the main portion of the beam to create a generally square wave graph of fluence versus radial position. FIG. 6 illustrates how this is accomplished with one embodiment of the present invention. The walls 72 of chamber 38 are made to be highly reflective of the particular wavelength of radiation. In the preferred embodiment the wavelength is 1064 nanometers and surface 72 is provided with a highly reflective gold surface. As suggested in FIGS. 5A and 6, the diverging laser beam 74 not only passes directly through window 46 but the edge portions of the beam are reflected off the walls 72 back into the main portion of the beam to create a generally equalized fluence level. Other optical arrangements can be used to help equalize the fluence applied to skin surface 6. For example, various devices called optical integrators or beam homogenizers are well known in the art of laser material processing. The simplicity of the present device is possible because the exit aperture, by virtue of being close to the contact surface 34, is located close to the target surface.

In another embodiment, shown in FIG. 7, reflective chamber 38, exit aperture 44 and protective window 46A are spaced much further from the skin surface to, for example, give the practitioner a better view of the treatment area 73 through a view port 75. View port 75 may be an open region, as illustrated, or it could include, for example, transparent and/or reflective members to permit direct or indirect viewing of area 73. In this case, a lens system 77 may be used between exit aperture 44 and window 46A to make an image of the exit aperture on the skin surface at treatment area 73. With this approach, the size of the exit aperture need not be the same size as the treatment area 73 on the skin surface. Moreover, because the end of the optical fiber 42 is spaced farther from the skin surface, it may be possible to rest contact surface 34 on the patient's skin. The size of treatment area 73 could be made variable by proper selection of the focal length of lens system 77 and the distance between exit aperture 44 and the lens system. This would be useful when it is desired to use the device for other treatments, such as the treatment of varicose veins, or the like.

In one mode of operation, controller 31 may be configured such that laser source 29 emits laser pulses continuously at a constant repetition rate. For example, the repetition rate is typically between approximately 1 Hz and approximately 12 Hz, and preferably between 2 Hz and 7 Hz. As can be appreciated, for more highly skilled practitioners, it is possible to use a higher repetition rate (e.g., 10 Hz to 12 Hz) to deliver the therapeutic laser energy to the sebaceous glands. Controller 31 may comprise software, hardware, or a combination thereof to control the duration of the pulses and delay of the sequence of the pulses. Once the pulse duration and repetition rate is selected, the practitioner may hold the handpiece over the patient's skin and move it at a substantially constant velocity equal to the product of exposure-area length time repetition rate that is desired. This will maximize the rate at which the treatment proceeds while still providing adequate time for the skin to cool. Optionally, the controller 31 may be configured to determine an intended total elapsed treatment time or the number of pulses to achieve a desired dose based on the laser parameters selected by the practitioner.

Part of the selection of the repetition rate is based on the theory of selective photo thermolysis in which a laser-pulse duration should be selected to match the thermal relaxation time of the target tissue (e.g., sebaceous gland). This theory is used in conjunction with the fact that high peak powers are desired because of the large amount of energy can be delivered in a short amount of time so as to allow a temperature spike in the target tissue, while minimizing damage to the surrounding tissue. As noted above, a peak power of at least 10 kW is desirable. Thus, it is preferred to use shorter pulse durations with high peak powers and to selectively adjust the duration according to the target tissue to minimize or eliminate damage to epidermis 10 while not sacrificing heat transfer to target tissue. In regards to treatment of acne, the high peak power, shorter pulse durations have been found to be effective because the short thermal relaxation time of the sebaceous glands and other small targeted structures.

With this in mind, the methods and systems of the present invention typically use a peak power near infrared (NIR) laser energy to thermally treat a target tissue, and in particular a sebaceous gland to treat acne vulgaris. It is believed that a wavelength in the range of about 800 nanometers to 1200 nanometers are suitable for use with the present invention. For one embodiment, a wavelength of 1064 nanometers has been chosen. The choice of a 1064 nanometer laser is beneficial for many reasons. It permits treating of patient having darker pigmented skin than the shorter wavelength lasers commonly used. The 1064 nanometer laser is relatively efficient, requires no special cooling and has the ability to create high pulse energy in low duty cycle pulses without large power-consuming support systems. Further the 1064 nanometer laser can use flash lamp excitation which can be engineered at a fraction of the cost of high peak power diode lasers.

Treatments of the present invention make use of transient heating of sebaceous gland absorbers (e.g., melanin and hemoglobin) and bulk heating of the surrounding dermal tissue, to raise the temperature of the sebaceous gland to a predetermined therapeutic temperature. Bulk heating of the dermal tissue is achieved through weak absorption of the NIR laser light and thermal diffusion from the sebaceous gland or other absorbers to other absorbing structures in the epidermis and dermis. Transient heating of the sebaceous gland absorbers is carried out by high absorption of the NIR light followed by rapid thermal relaxation. The heat buildup in the sebaceous gland from the delivery of the high peak power NIR light rapidly decays due to the small size of the sebaceous gland absorbers. Such rapid thermal relaxation makes it difficult to sufficiently raise the temperature of the sebaceous gland to a sufficient temperature to treat acne vulgaris. Thus, the practitioner must select a proper fluence, repetition rate and pulse duration to achieve the sufficient temperature while ensuring that damage to the surrounding dermal tissue is kept to an acceptable level.

The transient heating and bulk heating effects are schematically illustrated in FIGS. 8A and 8B which provide a simplified thermal profile at a strong absorber of NIR light in skin and a thermal profile for a dermal element (e.g., epidermal or dermal tissue) that is remotely located form the strong absorber, respectively. The strong absorber in the skin may be melanin, hemoglobin, water, the sebaceous gland, or other absorbing structures in the epidermis and dermis. As can be appreciated, weak absorbers in the skin, such as lipo (i.e., fat), may also contribute to the transient and bulk heating effects.

FIG. 8A illustrates a temperature rise at or near the site of the NIR strong absorber. Pulsing of the NIR light causes a rise in the temperature at and around the strong absorber from its initial temperature, T Initial (usually 37° C.). Continued pulsing of the NIR light causes a gradual rise in the surrounding bulk dermal tissue (FIG. 8B) and spikes of temperature increases followed by a rapid relaxation in between pulses at the strong absorber. The rapid thermal relaxation from the heat decay brings the temperature of the absorber back down to a "pedestal" temperature that is coincident with the temperature of the immediately surrounding dermal tissue. Temperature T1, which may be between approximately 40° C. and approximately 50° C., is a therapeutic temperature that is reached in the temperature profile only during thermal "spiking." The therapeutic effect requires the thermal "pedestal" from bulk heating as well as the transient local temperature spikes to raise the temperature of the absorber above temperature T1. In order to treat acne vulgaris or the other dermatologic conditions described herein, temperature T1 should be maintained for a predetermined time, typically between 0 seconds and 30 seconds It should be appreciated however, that the predetermined time will vary depending on temperature T1.

As shown in FIG. 8B, temperature T2 is a second therapeutic temperature that is reached throughout the immediate and remote bulk of the dermal tissue and relies on the transient heating of the absorbers only in the sense that local transient heating contributes to the overall bulk heating of the dermal tissue through diffusion. The tissue that is remote from the strong absorbers are not raised to the temperature T1, and thus are not raised to a temperature that is sufficient to achieve the desired result (e.g., treat acne vulgaris), nor is the remote tissue raised to a temperature high enough to cause permanent thermal damage. Depending on the specific procedure being performed (e.g., pore reduction, wrinkle smoothing, skin texturizing, reduction of rosacea, diffuse redness, striae, scarring, or treatment of acne), the practitioner may maintain the temperature T1 in each zone of treatment between approximately 1 second to approximately five minutes.

Figure 9A:
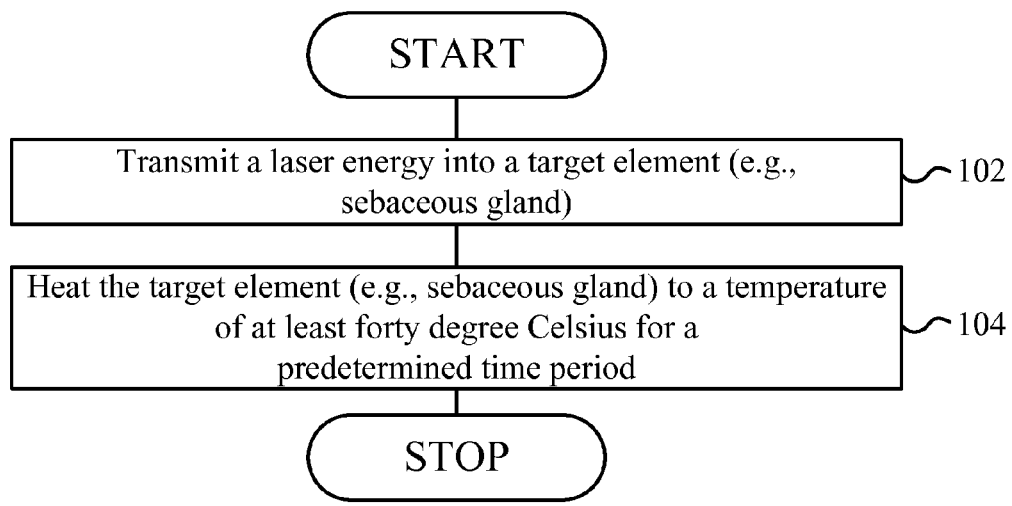
FIG. 9A schematically illustrates a simplified method of the present invention.
Figure 9B:
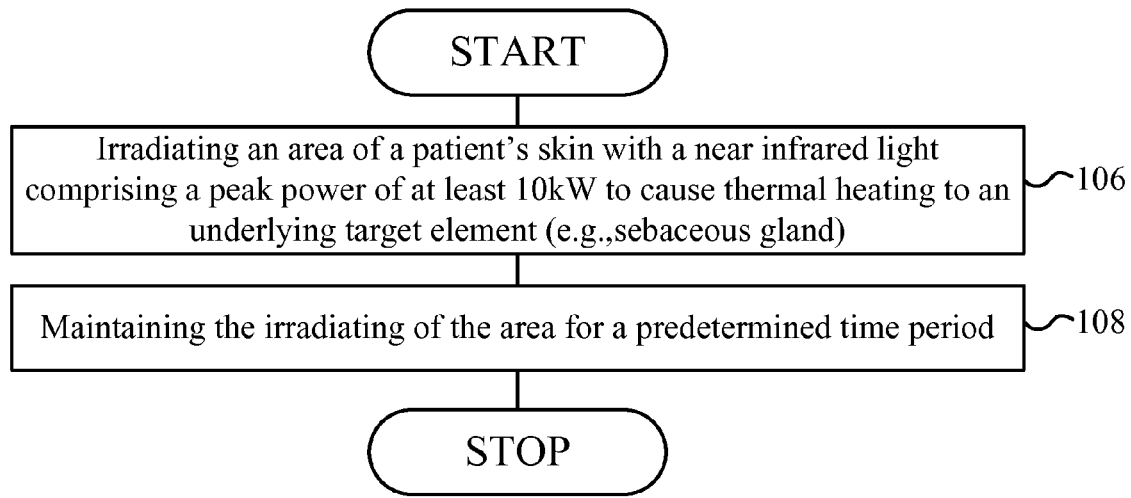
FIG. 9B schematically illustrates another simplified method of the present invention.
Figure 9C:
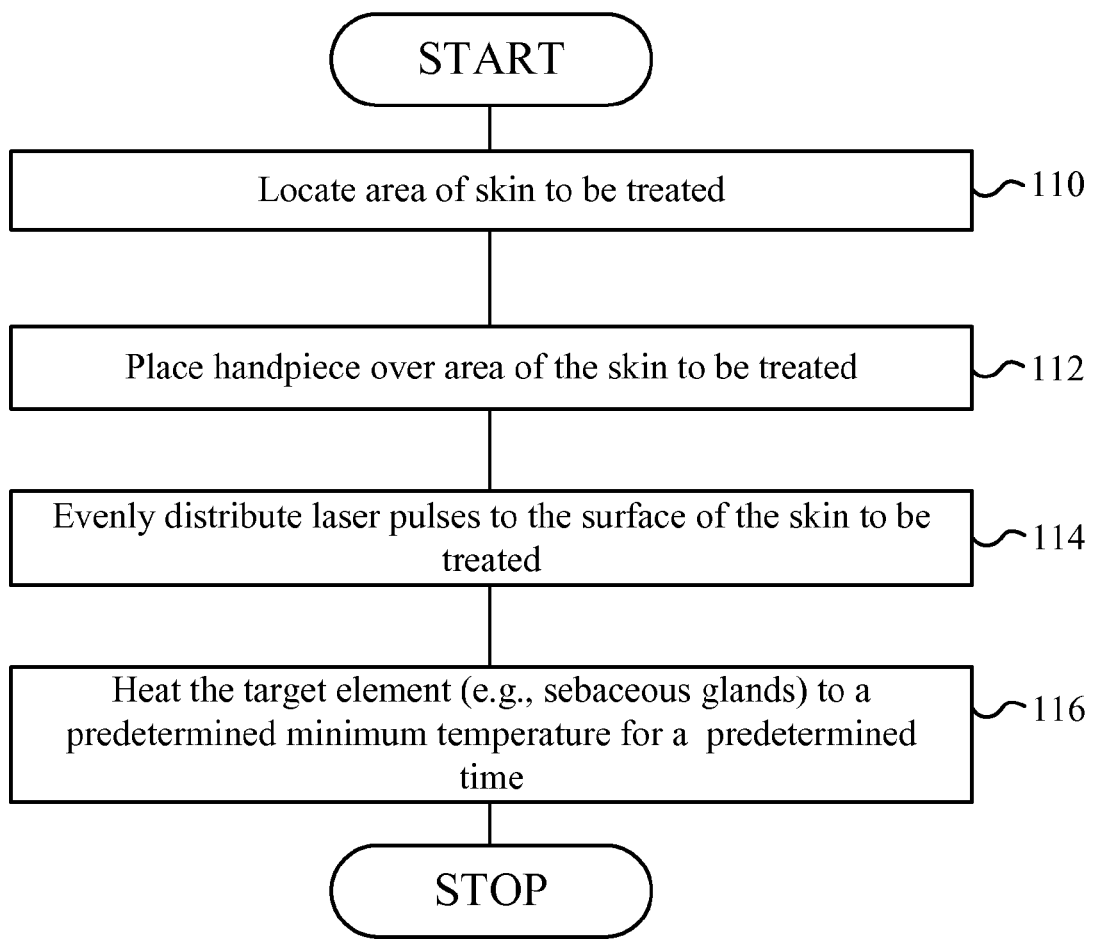
FIG. 9C schematically illustrates one detailed method of the present invention.

FIGS. 9A to 9C schematically illustrate some methods of the present invention. As illustrated in FIG. 9A, a laser energy is transmitted into a target tissue or element, such as the sebaceous gland, step 102. The laser energy heats the target element or tissue (e.g., sebaceous gland) to a temperature of at least forty degrees Celsius for a predetermined time period, step 104. Applicants believe that heating of the sebaceous gland to above forty degrees Celsius effects the *p. acnes* population, the rate of sebum secretions in the sebaceous gland, and/or may damage or destroy the sebaceous gland.

As described above, the laser energy is typically delivered in pulses of high peak powered laser energy so as to allow delivery of a high amount of energy in a short period of time so as to quickly raise the temperature of the target tissue to above forty degrees Celsius, while maintaining the surrounding tissue below a safe temperature. It should be appreciated, however, that in some embodiments instead of pulsing the laser energy, it may be possible to pre-cool and/or cool the epidermis during the laser treatment with cooling surface 34 and use a continuous delivery of laser energy.

As illustrated in FIG. 9B, in another method, an area of a patient's skin is irradiated with a near infrared light having a peak power of at least 10 kW to cause thermal heating of an underlying target element or tissue (e.g., sebaceous gland), step 106. The irradiating of the area is maintained for a predetermined time period, step 108, so as to achieve the desired result (e.g., treat acne vulgaris).

Similar to above, the peak power may be pulsed and used to raise the temperature of the sebaceous gland to a therapeutic temperature that effects acne vulgaris. Such a method may have similar parameter ranges (e.g., pulse duration, fluence, repetition rate, and the like), as described above.

In a specific embodiment of a non-ablative laser treatment illustrated in FIG. 9C, the operator first determines the area to be treated, step 110. Optionally, the area to be treated may be prepared for the laser treatment by removing make-up, shaving the area, spraying of a mist of water onto the skin surface, and the like.

Once the treatment area is selected, the laser parameters may be selected, depending on the type of procedure being performed (e.g., hair removal, wrinkle reduction, skin texturing, pore reduction, acne treatment, or the like). The laser parameters typically include pulse duration (typically between a single shot and 12 Hz, fluence (typically between 8 $J/cm^2$ and 20 $J/cm^2$, spot size (typically 3 mm, 5 mm, 7 mm, and 10 mm), and repetition rate (typically between 2 Hz and 12 Hz). As can be appreciated, the practitioner's skill level may play a part in the parameters. For example, "beginner" practitioners may use a fluence of approximately 13 $J/cm^2$, while a more seasoned practitioner may use a higher fluence The laser parameters may be selected using appropriate inputs 37 on the user interface. In other embodiments, the laser parameters may be pre-selected by the manufacturer of the laser system or pre-selected based on prior laser treatments on the patient.

A front end 30 of the handpiece 22 may be placed over an initial target area on the patient's skin, step 112. Typically a portion of the face (or other area of the body) to be treated is typically treated in sections of approximately 4 cm by 5 cm, or an equivalent area. As can be appreciated, the actual dimensions of the treatment area may vary, as defined by the location of the area on the face or body. To ensure full treatment of the entire area of the skin without missing areas or having excessive overlaps in area, the skin area may be temporarily marked with a set of lines or a grid to help guide device 22. One section of the face is treated at a time.

Front end 30 of handpiece is then placed over the initial target area on the patient's skin and spaced approximately 1 cm to 2 cm from the surface of the skin. Delivery of the laser energy can be activated by depressing a button 84 on handpiece (FIG. 3F) or activation of a footswitch. Handpiece 22 may then be moved back and forth over the initial area (both top to bottom and left to right) such that there is a substantially even distribution of laser pulses and a substantially even distribution of thermal treatment to the target elements in the tissue (e.g., sebaceous gland), step 114. By substantially evenly distributing the laser pulses, the heat build in the target elements up should be uniform and comfortable to the patient, while reducing the localized hot spots on the skin. The thermal damage is intended to thermally effect the target tissue to achieve the desired result. In the illustrated embodiment, the thermal damage is intended to effect the sebaceous gland and/or *p. acne* bacterium that is present in the sebaceous gland, step 116.

In one embodiment, a treatment speed would allow for approximately two passes from left to right and back again across a 4 cm to 5 cm length in a one second period. While the repeated left to right motions are being made, the practitioner may move the laser spot up or down so as to avoid overlapping the laser passes.

The area of treatment is typically treated with approximately 400 pulses to approximately 500 pulses, although the amount of pulses may vary depending on the selected laser parameters and the area of the skin that is treated. Optionally, the number of pulses that are delivered to the patient's skin may be counted and a signal may be generated by the system 21 that informs the practitioner of the number of pulses that have been delivered. For example, an audible tone, such as a "water drop" may be delivered every 100 pulses to inform the practitioner of number of pulses that has been delivered. The computer system may also be configured to monitor a temperature of the patient's skin and/or prevent delivery of the laser pulses once a predetermined or user specified number of pulses has been delivered or a threshold temperature has been reached. For example, once 500 pulses have been delivered to the target area, the user may be forced to activate a button or footswitch to continue delivering laser pulses to the skin in the target area.

Figure 10:
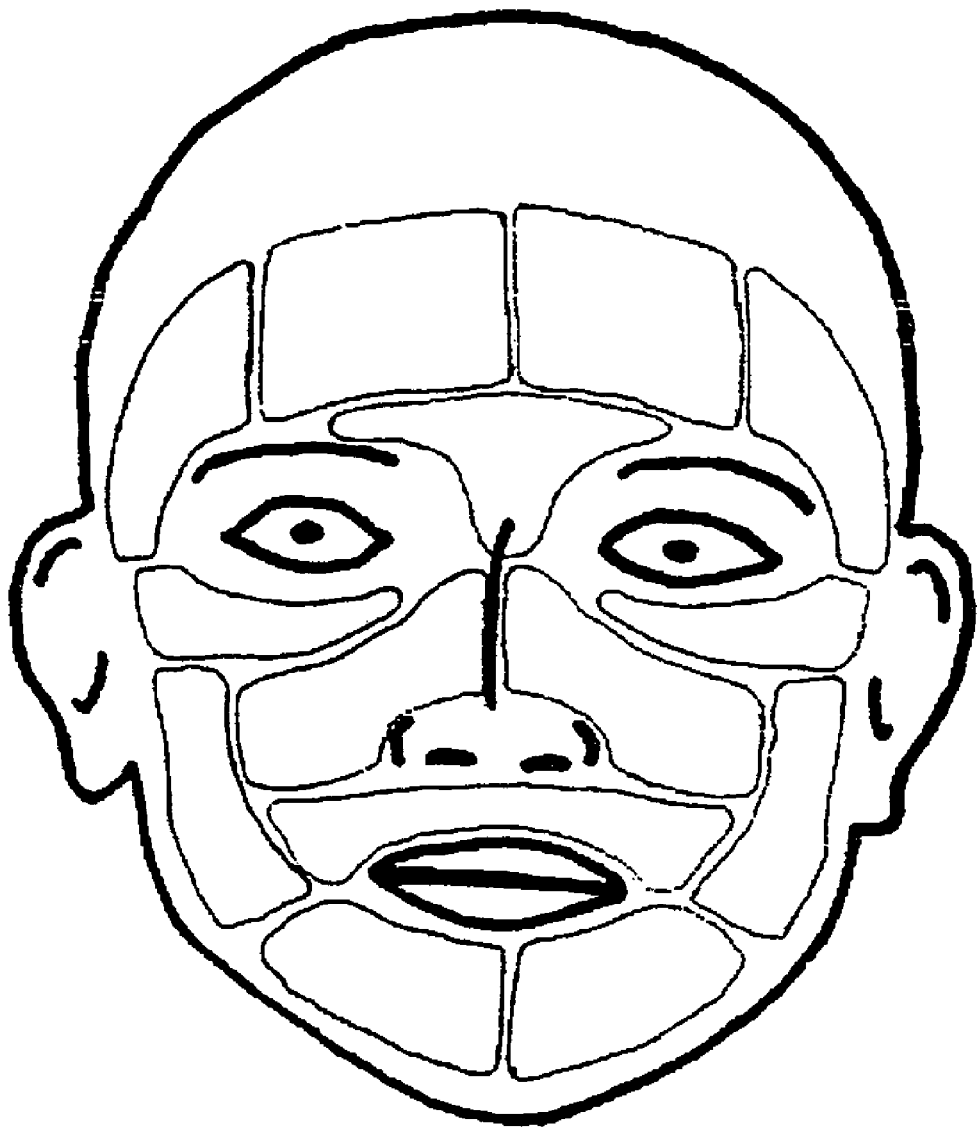
FIG. 10 illustrates a sample segmentation of the face for acne treatment.

FIG. 10 illustrates a sample segmentation of the face for acne treatment. The laser energy may be delivered to at least one of the segments during the laser acne treatment. When delivering laser energy to segments around the patient's eyes, patients should wear eye protection so as to prevent ocular damage from the laser light. From experimental results, applicants have found that treatments of full faces may require approximately 7000 pulses of laser energy, in which 2400 pulses are delivered on each side of the face below the corner of the eyes to the ears and approximately 1100 pulses on each side of the forehead above the corner of the eyes. As can be appreciated, the number of pulses will vary depending on the particular patient, the selected laser parameters, and the like. A total amount of four to six treatments may be performed to treat acne vulgaris. Typically, the laser treatments may be performed every two to four weeks.

Although the above provides a complete and accurate description of specific embodiments of the present invention, it should be appreciated that the above examples should not limit the scope of the present invention and modifications and changes can be made that are still within the scope of the invention. For example, although specific reference has been made to treating acne with a specific wavelength of light, any exposed tissue may be treated with light having a larger or smaller wavelength in accord with the above described invention. Moreover, while not specifically described, any of the methods described herein may use a cooling surface to cool the patient's skin during delivery of the laser energy into the sebaceous gland. In such methods, the laser energy may be pulsed of delivered continuously.

While the above description focuses on treating of the sebaceous gland for acne treatment, the methods of the present invention may also be used for photothermal therapy for wrinkle reduction, skin texturing, and pore size reduction. For example, strong absorption by water or other chromophores in the epidermis may produce a temperature rise in the epidermis that may give rise to wound healing or other processes which produce skin tightening or collagen production, which in turn produces a cosmetically desirable effect on skin texture. Such methods may be carried out using similar methods described herein. Therefore, the scope of the invention is limited solely by the following claims.

What is claimed is:

1. A method of improving the appearance of an area of the skin using light from a Nd:YAG laser, said light being delivered through a handpiece, said method comprising the steps of:

generating a series of laser pulses from the laser, said laser pulses having a pulse width of between 100 microseconds to one millisecond and a peak power of at least 10 kilowatts and a repetition rate in a range of between approximately 2 Hz and 12 Hz;

spacing the handpiece from the surface of the skin; and delivering at least 400 laser pulses to the area of skin to be treated from the handpiece with a spot size on the tissue between 3 mm and 10 mm and with a fluence between 8 J/cm$^2$ and 20 J/cm$^2$ on the surface of the skin, the application of said laser pulses resulting in an improvement in the appearance of the skin without ablating the skin.

2. The method as recited in claim 1 further including the step of moving the handpiece over the area of the skin to be treated for at least a portion of the time the pulses are being delivered.

3. The method of claim 1, wherein pulses are applied to the treated area of tissue continuously for a time period in the range of approximately 1 minute to 5 minutes.

4. The method of claim 1, wherein the application of the laser pulses effects a reduction of diffuse redness in the skin.

5. The method of claim 1, wherein the application of laser pulses effects a reduction in a size of a pore.

6. The method of claim 1, wherein the application of laser pulses effects a reduction in acne.

7. The method of claim 1, wherein the application of laser pulses effects a reduction in a size of a wrinkle.

8. The method of claim 1, wherein the handpiece is spaced from the tissue about 1 to 2 centimeters.

9. The method of claim 1, wherein the laser pulses are delivered without cooling of the skin.

10. The method of claim 1 further including the step of monitoring the temperature of the skin being treated and modifying the output of the laser in response thereto.

11. A method of improving the appearance of an area of the skin using light from a Nd:YAG laser comprising the steps of:

generating a series of laser pulses from the laser, said laser pulses having a pulse width of between 100 microseconds to one millisecond and a peak power of at least 10 kilowatts; and delivering at least 400 laser pulses to the area of skin to be treated, the application of said laser pulses resulting in an improvement in the appearance of the skin without ablating the skin.

12. The method of claim 11, wherein the spot size of the pulses at the tissue are between 3 mm and 10 mm.

13. The method of claim 11, wherein each of the laser pulses has a fluence between 8 J/cm$^2$ and 20 J/cm$^2$ on the surface of the skin.

14. The method of claim 11, wherein the pulses of light are generated at a repetition rate in a range of between approximately 2 Hz and 12 Hz.

15. The method of claim 11, wherein pulses are applied to the treated area of tissue continuously for a time period in the range of approximately 1 minute to 5 minutes.

16. The method of claim 11, wherein the application of the laser pulses effects a reduction of diffuse redness in the skin.

17. The method of claim 11, wherein the application of laser pulses effects a reduction in a size of a pore.

18. The method of claim 11, wherein the application of laser pulses effects a reduction in acne.

19. The method of claim 11, wherein the application of laser pulses effects a reduction in a size of a wrinkle.

20. The method of claim 11, wherein the laser pulses are delivered without cooling of the skin.

21. The method of claim 11 further including the step of monitoring the temperature of the skin being treated and modifying the output of the laser in response thereto.

22. A laser treatment system comprising:

a flashlamp pumped Nd:YAG laser;

a power supply for energizing the flashlamp to cause the laser to generate laser output;

a treatment handpiece;

an optical fiber for delivering the laser output to the handpiece; and a controller for delivering signals to the power supply to cause the laser to generate a series of laser pulses, said laser pulses having a pulse width of between 100 microseconds to one millisecond and a peak power of at least 10 kilowatts and a repetition rate in a range of between approximately 2 Hz and 12 Hz, said laser pulses being delivered to tissue through the handpiece for treatment of the skin.

23. A system as recited in claim 22 further comprising a sensor carried by the handpiece for monitoring the temperature of the skin being treated and wherein the output of the sensor is coupled to the controller for modifying the laser output in response to the monitored temperature.

* * * * *